United States Patent [19]
Garza et al.

[11] Patent Number: 5,804,340
[45] Date of Patent: Sep. 8, 1998

[54] PHOTOMASK INSPECTION METHOD AND INSPECTION TAPE THEREFOR

[75] Inventors: Mario Garza, Sunnyvale; Keith K. Chao, San Jose, both of Calif.

[73] Assignee: LSI Logic Corporation, Milpitas, Calif.

[21] Appl. No.: 772,309

[22] Filed: Dec. 23, 1996

[51] Int. Cl.⁶ .................................................. G03F 9/00
[52] U.S. Cl. ................................................. 430/5; 382/144
[58] Field of Search ........................ 430/5, 22; 382/144

[56] References Cited

U.S. PATENT DOCUMENTS

| | | | |
|---|---|---|---|
| 4,962,541 | 10/1990 | Doi et al. .................................. | 382/144 |
| 5,287,290 | 2/1994 | Tabara et al. ............................. | 382/144 |
| 5,475,766 | 12/1995 | Tsuchiya et al. ......................... | 382/144 |

*Primary Examiner*—S. Rosasco
*Attorney, Agent, or Firm*—Hickman & Martine, LLP

[57] ABSTRACT

A method of inspecting a photomask for use in photolithography which accounts for the rounding of corners of features that occurs during manufacture of the photomask. A data tape used in the preparation of the photomask is first provided. An inspection tape is then prepared by modifying the data on the data tape to account for rounding of the features during preparation of the photomask. Finally, an inspection device is used to compare features on the photomask to data on the inspection tape corresponding to such features.

15 Claims, 4 Drawing Sheets

PHOTOMASK INSPECTION METHOD AND INSPECTION TAPE THEREFOR

BACKGROUND OF THE INVENTION

The present invention relates to photolithography techniques. More particularly, the invention relates to a method of inspecting a photomask for use in photolithography, a method of preparing an inspection tape for use in inspecting a photomask used in photolithography, and an inspection tape for use in inspecting a photomask used in photolithography.

Photolithography involves selectively exposing regions of a resist coated silicon wafer to a radiation pattern, and developing the exposed resist to protect regions of wafer layers (e.g., regions of substrate, polysilicon, or dielectric).

An integral component of a photolithographic apparatus is a photomask or "reticle" which includes a pattern corresponding to features at one layer in an IC design. The photomask typically includes a transparent glass plate covered with a patterned light blocking material such as chromium. The photomask is placed between a radiation source producing radiation having a desired wavelength and a focusing lens which may form part of a "stepper" apparatus. A resist coated silicon wafer is placed below the stepper. When radiation from the radiation source is directed onto the photomask, light passes through the portions of the glass plate not covered with chromium and projects onto the resist coated silicon wafer. In this manner, an image of the photomask is transferred to the resist coated on the silicon wafer.

Photomasks are presently manufactured by depositing chromium on a transparent glass plate, coating the chromium with a resist, printing a pattern on the resist using a pattern generator, developing the resist, and subjecting the photomask to chemical processing to remove everything but the desired pattern of chromium from the glass plate. In the printing step, the pattern generator directs an electron beam based on information provided on a data tape which includes data corresponding to the features to be printed on the resist.

After being manufactured, the photomask is inspected for defects using a conventional inspection device. The inspection device optically detects the features printed on the photomask and compares such printed features with the corresponding data on the data tape used to make the photomask. When a mismatch between the photomask and the data tape occurs, the inspection device signals that a defect has been detected.

One of the problems associated with the present photomask manufacturing technology is that the corners of features are subject to rounding due to electromagnetic wave effects and chemical processing effects. This rounding of corners, which is more prominent when the features are small (0.5 micron or smaller at the photomask level), makes inspection of the photomask difficult and time consuming because the inspection device faults as a result of the large number of rounded corners detected.

Attempts have been made to prevent the inspection device from signaling a defect each time a rounded corner is detected by lowering the sensitivity of the optical detectors in the inspection device. This solution is unsatisfactory, however, because lowering the global sensitivity of the inspection device creates a significant risk that a real defect in the photomask will go undetected. Thus, what is needed is a method of inspecting a photomask that will prevent the inspection device from signaling a defect at rounded corners without sacrificing the global sensitivity of the inspection device.

SUMMARY OF THE INVENTION

The present invention fills this need by providing a method of inspecting a photomask which accounts for the rounding of corners of features that occurs during manufacture of the photomask and, consequently, prevents the inspection device from signaling a defect each time a rounded corner is detected. In one aspect, the present invention provides a method of inspecting a photomask for use in photolithography in which a data tape used in the preparation of the photomask is first provided, the data tape having data corresponding to features on the photomask thereon. An inspection tape is then prepared by modifying the data on the data tape to account for rounding of the features during preparation of the photomask. Finally, an inspection device is used to compare features on the photomask to data on the inspection tape corresponding to such features.

In a preferred embodiment, the modified data includes data corresponding to inside corners and outside corners. The data corresponding to inside corners is modified by adding pixels thereto. The data corresponding to outside corners is modified by removing pixels therefrom.

In another aspect, the present invention provides a method of preparing an inspection tape for use in inspecting a photomask for use in photolithography in which a data tape having data corresponding to features on a photomask thereon is first provided. The data on the data tape is then modified to account for rounding of the features during preparation of the photomask to obtain an inspection tape. In the course of inspecting the photomask, the features on the photomask detected by the inspection device are compared to data corresponding to such features on the inspection tape.

In a still further aspect, the present invention provides an inspection tape for use in inspecting a photomask used in photolithography. The data on the inspection tape corresponding to features on a photomask is modified relative to corresponding data on a data tape used in the preparation of the photomask to account for rounding of the features during preparation of the photomask.

These and other features and advantages of the present invention will become apparent upon reading the following detailed description and studying the various figures of the drawings.

DETAILED DESCRIPTION OF THE PREFERRED EMBODIMENTS

One aspect of the present invention is a method of inspecting a photomask for use in photolithography. In this method a data tape used in the preparation of the photomask is first provided. Such data tapes are known to those skilled in the art and have data corresponding to features on the photomask thereon. As described above, in the preparation of a photomask the data on the data tape is used by the pattern generator to direct an electron beam to print the desired features on the resist.

Figure 1:
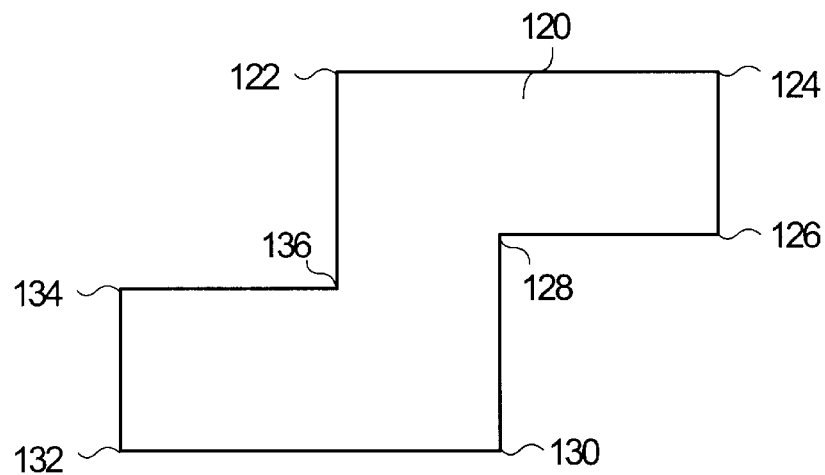
FIG. 1 illustrates the shape of an exemplary IC design pattern including a pair of right angle bends.
Figure 2:
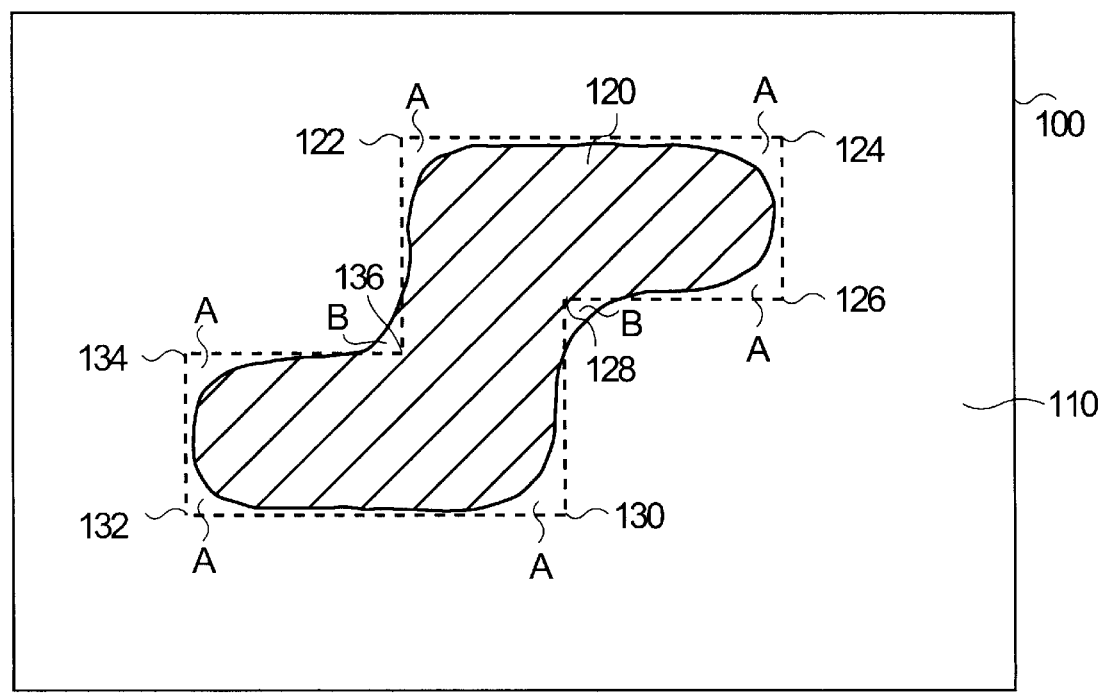
FIG. 2 shows a photomask having the IC design pattern of FIG. 1 outlined in, for example, chromium on a glass plate. The design pattern of FIG. 1 is shown as a dotted line to illustrate the rounding of corners during preparation of the photomask.

In accordance with the invention, an inspection tape is prepared by modifying the data on the data tape to account for rounding of the features during preparation of the photomask. FIG. 1 illustrates the shape of exemplary IC design pattern 120 which includes a pair of right angle bends. Design pattern 120 includes outside corners 122, 124, 126, 130, 132, and 134 and inside corners 128 and 136. FIG. 2 shows photomask 100 including design pattern 120 of FIG. 1 formed of chromium on transparent glass plate 110. In FIG. 2 the shape of design pattern 120 as shown in FIG. 1 appears as a dotted line to illustrate the rounding of corners during preparation of the photomask.

Figure 3:
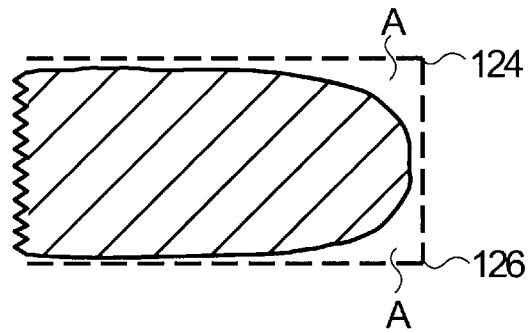
FIG. 3 is an exploded view of corners 124 and 126 of IC design pattern 120 shown in FIG. 2.

As shown in FIG. 2, the rounded regions of chromium corresponding to outside corners 122, 124, 126, 130, 132, and 134 have retracted such that regions A within the dotted line corresponding to the intended shape of design pattern 120 are not covered with chromium. This rounding effect by retraction can be seen more clearly in FIG. 3, which is an exploded view of outside corners 124 and 126 shown in FIG. 2.

Figure 4:
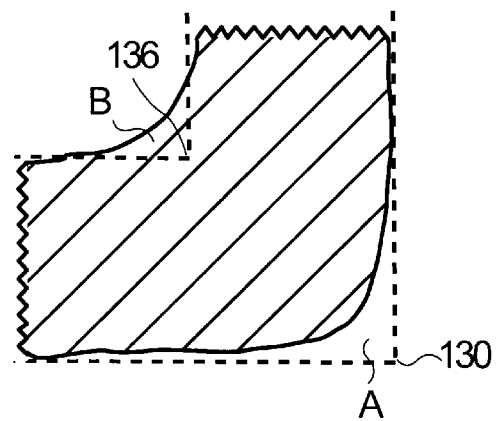
FIG. 4 is an exploded view of corners 130 and 136 of IC design pattern 120 shown in FIG. 2.

As further shown in FIG. 2, the rounded regions of chromium corresponding to inside corners 128 and 136 have expanded such that regions B outside the dotted line corresponding to the intended shape of design pattern 120 are covered with chromium. This rounding effect by expansion can be seen more clearly in FIG. 4, which is an exploded view of inside corner 136 and outside corner 130 shown in FIG. 2.

The objective of the data modification in the preparation of the inspection tape is to mimic the rounded shape of the corners obtained in a processed photomask so that the inspection device does not signal a defect each time it detects a rounded corner. Thus, in the case of outside corners, the data on the data tape must be modified to account for the lack of chromium in regions A shown in FIG. 2. This can be accomplished by removing a suitable number of pixels from the data on the data tape corresponding to the portions of outside corners that are not expected to be covered with chromium after processing, i.e., regions A shown in FIG. 2. In the case of inside corners, the data on the data tape must be modified to account for the presence of chromium in regions B shown in FIG. 2. This can be accomplished by adding a suitable number of pixels to the data on the data tape corresponding the areas just outside inside corners that are covered with chromium after processing, i.e., regions B shown in FIG. 2.

The data modification required in the preparation of the inspection tape can be accomplished by, for example, a suitable software code. The software code must sort through the data on the data tape corresponding to features on the photomask and modify the data corresponding to outside corners by removing a suitable number of pixels therefrom and modify the data corresponding to inside corners by adding a suitable number of pixels thereto. Those skilled in the art are capable of generating such a software code.

Once prepared, the inspection tape is installed in an inspection device and used to inspect a processed photomask. The inspection device optically detects features on the photomask and compares such features to data on the inspection tape corresponding to such features. As the data on the inspection tape has been modified to account for the rounding of features during processing of the photomask, the inspection device does not signal a defect each time a rounded corner is detected but instead signals a defect only when a more serious defect is detected.

Figure 5A:
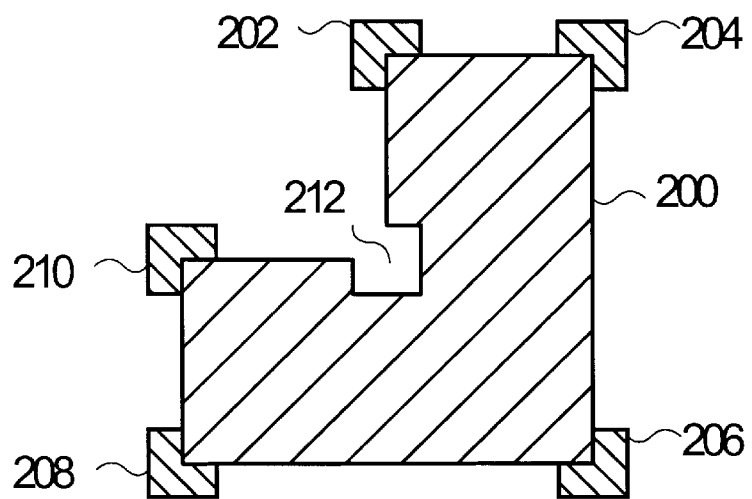
FIG. 5A illustrates the shape of an exemplary IC design pattern including serifs.

The method of inspecting a photomask of the present invention is particularly suited to inspecting photomasks including small features such as, for example, serifs and step functions because rounding of corners is more prominent when the features are small (0.5 micron or smaller at the photomask level). FIG. 5A illustrates the shape of exemplary IC design pattern 200 having an elbow shape and including serifs 202, 204, 206, 208, 210, and 212 at the corners thereof. Such serifs are used in a technique known as optical proximity correction ("OPC") to overcome the distorting effects of diffraction and scattering when radiation such as light passes through the photomask. Serifs 202, 204, 206, 208, and 210 are small appendage-type addition regions known as "out" serifs. Serif 212 is a small appendage-type subtraction region known as an "in" serif.

Figure 5B:
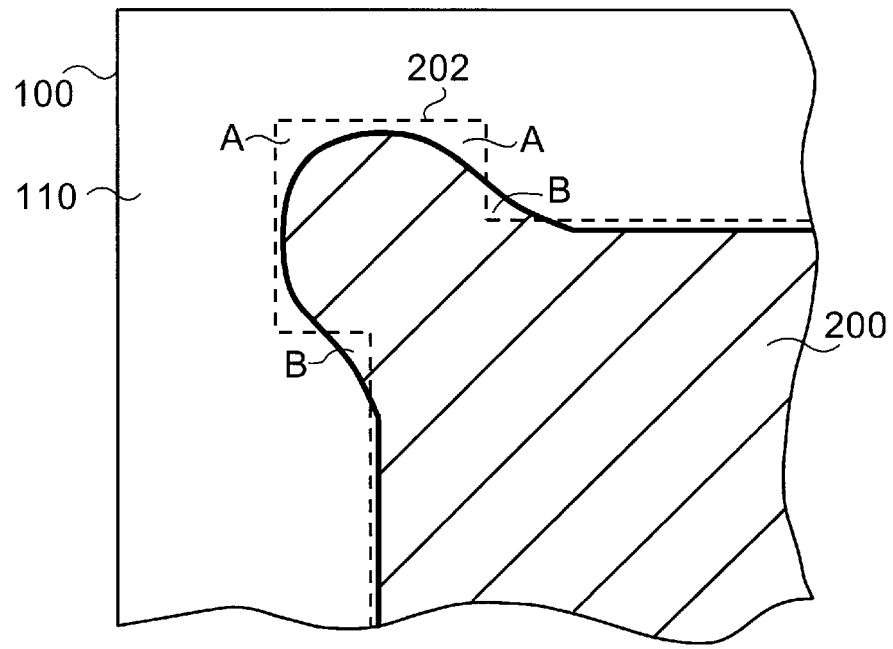
FIG. 5B shows a first exploded partial view of a photomask having the IC design pattern of FIG. 5A outlined in, for example, chromium on a glass plate. The design pattern of serif 202 shown in FIG, 5A is shown as a dotted line to illustrate the rounding of corners during preparation of the photomask.

FIG. 5B shows a first exploded partial view of photomask 100 including design pattern 200 of FIG. 5A formed of chromium on transparent glass plate 110. In FIG. 5B the shape of the design pattern of serif 202 as shown in FIG. 5A appears as a dotted line to illustrate the rounding of corners that occurs at "out" serifs during preparation of the photomask. To prevent the inspection device from signaling a defect each time an "out" serif is inspected, a suitable number of pixels must be removed from the data on the data tape corresponding to regions A shown in FIG. 5B. In addition, a suitable number of pixels must be added to the data on the data tape corresponding to regions B shown in FIG. 5B.

Figure 5C:
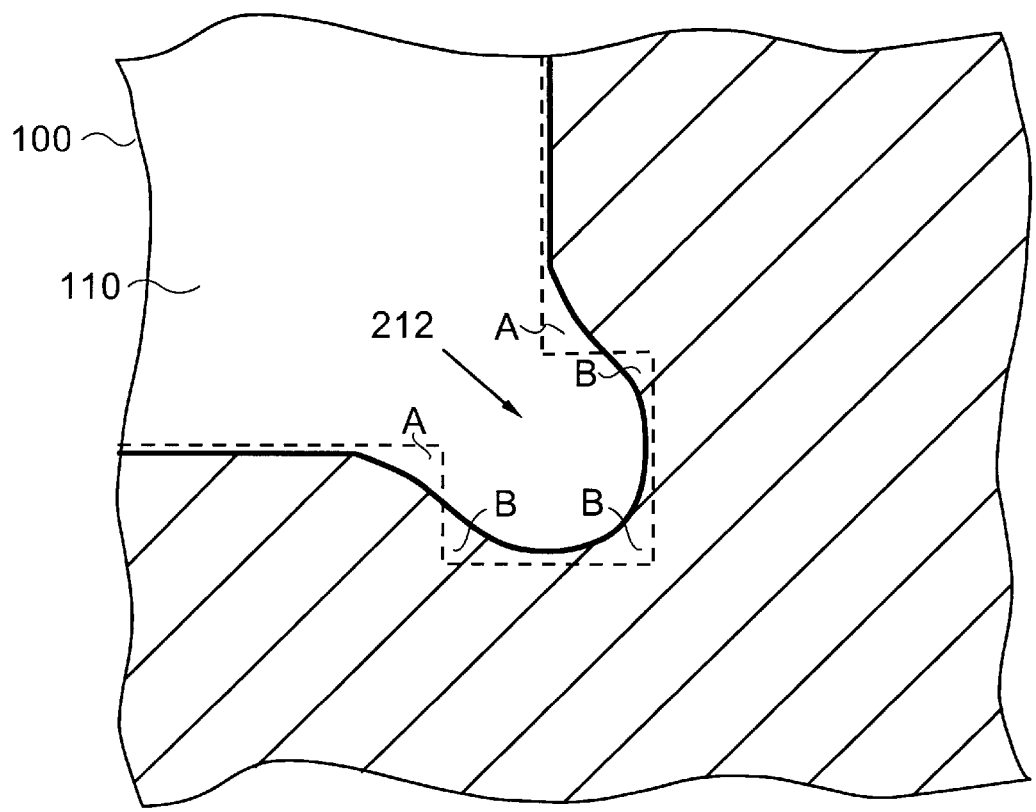
FIG. 5C shows a second exploded partial view of a photomask having the IC design pattern of FIG. 5A outlined in, for example chromium on a glass plate. The design pattern of serif 212 shown in FIG. 5A is shown as a dotted line to illustrate the rounding of corners during preparation of the photomask.

FIG. 5C shows a second exploded partial view of photomask 100 including design pattern 200 of FIG. 5A formed of chromium on transparent glass plate 110. In FIG. 5B the shape of serif 212 as shown in FIG. 5A appears as a dotted line to illustrate the rounding of corners that occurs at "in" serifs during preparation of the photomask. To prevent the inspection device from signaling a defect each time an "in" serif is inspected, a suitable number of pixels must be removed from the data on the data tape corresponding to regions A shown in FIG. 5C. In addition, a suitable number of pixels must be added to the data on the data tape corresponding to regions B shown in FIG. 5C.

Figure 6:
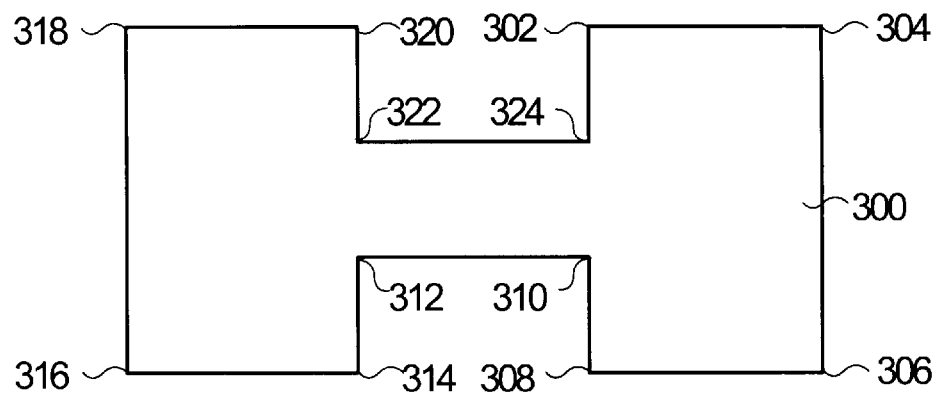
FIG. 6 illustrates the shape of an exemplary IC design pattern including a step function.

FIG. 6 illustrates the shape of an exemplary IC design pattern 300 including four step functions resulting from the expansion of opposing ends of the narrow center strip to form the thicker outer portions. Such an IC design pattern is typically encountered in connection with the active area of a transistor. As shown in FIG. 6, IC design pattern 300 includes outside corners 302, 304, 306, 308, 314, 316, 318, and 320 and inside corners 310, 312, 322, and 324. The inspection of a photomask including a step function such as the one defined by inside corner 324 and outside corner 302 is problematic, especially at small feature sizes, because the rounding effects associated with these corners occur right next to one another.

Figure 7:
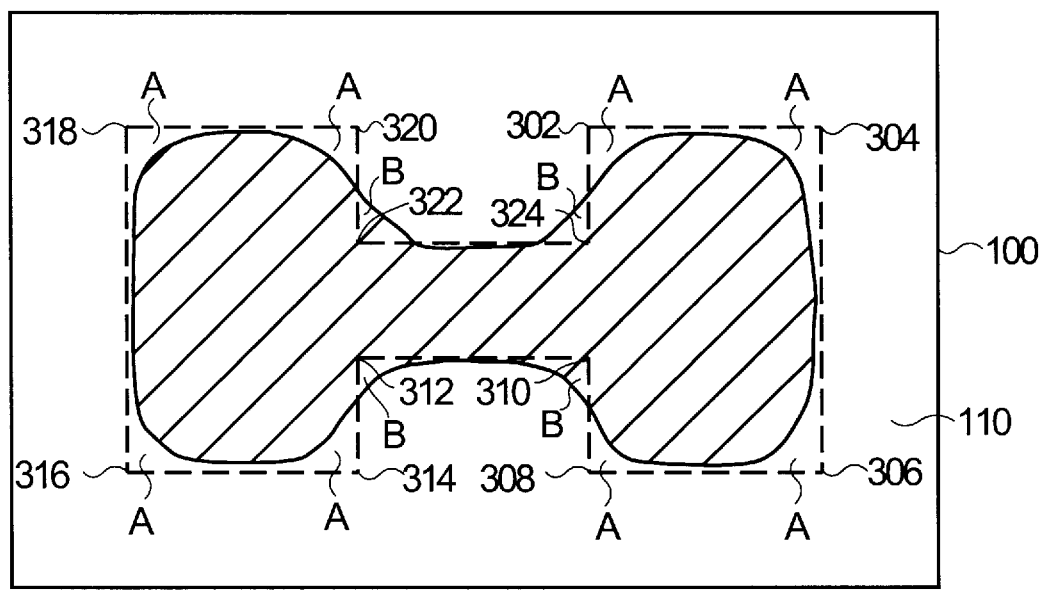
FIG. 7 shows a photomask having the IC design pattern of FIG. 6 outlined in, for example, chromium on a glass plate. The design pattern of FIG. 6 is shown as a dotted line to illustrate the rounding of corners during preparation of the photomask.

FIG. 7 shows photomask 100 including design pattern 300 of FIG. 6 formed of chromium on transparent glass plate 110. In FIG. 7 the shape of design pattern 300 as shown in FIG. 6 appears as a dotted line to illustrate the compounding of the rounding of corners that occurs at step functions during preparation of the photomask. Considering, for example, the step function defined by inside corner 324 and outside corner 302, rounding of inside corner 324 occurs by expansion such that region B, which is located outside the dotted line representing the intended shape of design pattern 300, is covered with chromium. Rounding of outside corner 302 occurs by retraction such that region A within the dotted line representing the intended shape of design pattern 300 is not covered by chromium. At smaller feature sizes, inspecting a photomask including a step function using the conventional inspection technique invariably results in the inspection device signaling a defect because of the close proximity of regions A and B. By using the inspection method of the present invention, however, such step functions can be inspected without the inspection device signaling a defect because the data on the inspection tape has been modified to account for the rounding of the corners making up the step function.

Another aspect of the present invention is a method of preparing an inspection tape for use in inspecting a photomask used in photolithography. In this method a data tape having data corresponding to features on a photomask thereon is first provided, as described above. The data on the data tape is then modified to account for rounding of the features during preparation of the photomask to obtain the inspection tape. The methodology for modifying the data on the data tape to obtain the inspection tape is described above in connection with the description of the method of inspecting a photomask of the present invention.

A still further aspect of the present invention is an inspection tape for use in inspecting a photomask used in photolithography. The data on the inspection tape corresponding to features on a photomask is modified relative to corresponding data on a data tape used in the preparation of the photomask to account for rounding of such features during preparation of the photomask. The methodology for making the inspection tape is described above in connection with the description of the method of inspecting a photomask of the present invention. As explained above, the inspection tape of the present invention provides a data base for use in inspecting a photomask that reflects the actual shapes of features formed on the photomask. When the inspection tape is used in conjunction with an inspection device to inspect a photomask, the inspection device does not signal a defect each time a rounded corner is detected because the optically detected features on the photomask are compared to modified data corresponding to such features that takes into account the rounding of corners that occurs during preparation of the photomask.

Although the preferred embodiments of the present invention have been described in detail, it should be understood that the present invention may be embodied in many other specific forms without departing from the scope or spirit of the invention. Therefore, the present examples and embodiments are to be considered as illustrative and not restrictive, and the invention is not to be limited to the details given herein, but may be modified within the scope of the appended claims.

What is claimed is:

1. A method of inspecting a photomask for use in photolithography, said method comprising the steps of:

providing a data tape used in the preparation of a photomask, said data tape having data corresponding to features on said photomask thereon;

preparing an inspection tape by modifying said data to account for rounding of said features during preparation of said photomask on a reticle; and using an inspection device to compare features on said photomask to data on said inspection tape corresponding to such features.

2. The method of claim 1, wherein the modified data includes data corresponding to inside corners.

3. The method of claim 2, wherein the data corresponding to inside corners is modified by adding pixels thereto.

4. The method of claim 1, wherein the modified data includes data corresponding to outside corners.

5. The method of claim 4, wherein the data corresponding to outside corners is modified by removing pixels therefrom.

6. A method of preparing an inspection tape for use in inspecting a photomask manufactured on a glass plate used in photolithography, said method comprising the steps of:

providing a data tape having data corresponding to features on a photomask thereon; and modifying said date to account for rounding of said features during preparation of said photomask to obtain a modified inspection tape.

7. The method of claim 6, wherein the modified data includes data corresponding to inside corners.

8. The method of claim 7, wherein the data corresponding to inside corners is modified by adding pixels thereto.

9. The method of claim 6, wherein the modified data includes data corresponding to outside corners.

10. The method of claim 9, wherein the data corresponding to outside corners is modified by removing pixels therefrom.

11. An inspection tape for use in inspecting a photomask used in photolithography, the data on the inspection tape corresponding to features on a photomask being modified relative to corresponding data on a data tape used in the preparation of said photomask to account for anticipated rounding of said features during preparation of said photomask before being transferred to a substrate surface, said anticipated rounding is produced when said data is transferred from a digital form to the photomask that is manufactured on a reticle.

12. The inspection tape of claim 11, wherein the modified data includes data corresponding to inside corners.

13. The inspection tape of claim 12, wherein the data corresponding to inside corners is modified by adding pixels thereto.

14. The inspection tape of claim 11, wherein the modified data includes data corresponding to outside corners.

15. The inspection tape of claim 14, wherein the data corresponding to outside corners is modified by removing pixels therefrom.

* * * * *